(12) United States Patent
Bittner et al.

(10) Patent No.: US 12,351,853 B2
(45) Date of Patent: Jul. 8, 2025

(54) URETHANASES FOR THE ENZYMATIC DEGRADATION OF POLYURETHANES

(71) Applicant: COVESTRO INTELLECTUAL PROPERTY GMBH & CO. KG, Leverkusen (DE)

(72) Inventors: Natalie Bittner, Frechen (DE); Hartmut Nefzger, Pulheim (DE); Gesa Behnken, Cologne (DE); Gernot Jäger, Cologne (DE); Swantje Behnken, Sacramento, CA (US); Lukas Reisky, Cologne (DE)

(73) Assignee: Covestro Deutschland AG, Leverkusen (DE)

( * ) Notice: Subject to any disclaimer, the term of this patent is extended or adjusted under 35 U.S.C. 154(b) by 44 days.

(21) Appl. No.: 17/692,254

(22) Filed: Mar. 11, 2022

(65) Prior Publication Data

US 2022/0282287 A1    Sep. 8, 2022

Related U.S. Application Data

(62) Division of application No. 17/254,701, filed as application No. PCT/EP2019/065947 on Jun. 18, 2019, now abandoned.

(30) Foreign Application Priority Data

Jun. 21, 2018 (EP) .................................... 18179032

(51) Int. Cl.
    *C12P 7/18* (2006.01)
    *C12N 9/80* (2006.01)
    *C12P 7/44* (2006.01)

(52) U.S. Cl.
    CPC .................. *C12P 7/44* (2013.01); *C12N 9/80* (2013.01); *C12P 7/18* (2013.01); *C12Y 305/01075* (2013.01)

(58) Field of Classification Search
    CPC ........ A01N 25/10; C09D 5/1637; C12N 9/80; C12N 9/78; C12N 9/20; C12P 7/18; C12P 7/44; C12P 13/001; C12Y 305/01075; C12Y 301/01; C12Y 301/01003
    USPC .......................... 435/19, 196, 142, 128, 159
    See application file for complete search history.

(56) References Cited

U.S. PATENT DOCUMENTS 6,180,381 B1    1/2001    Montgomery et al.

FOREIGN PATENT DOCUMENTS

| EP | 0968300 A1 | 1/2000 |
|---|---|---|
| JP | 09-192633 A | 7/1997 |
| JP | 09-201192 A | 8/1997 |
| JP | 10-271994 A | 10/1998 |
| JP | 200655005 A | 3/2006 |
| WO | 98/36086 A1 | 8/1998 |
| WO | 2006/019095 A1 | 2/2006 |
| WO | 2007029630 A1 | 3/2007 |
| WO | 2013/134801 A2 | 9/2013 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Kisselev L., (Structure, 2002, vol. 10: 8-9.*
Witkowski et al., (Biochemistry 38:11643-11650, 1999.*
Akutsu et al. ( Applied and Environ Microbiol 1998, pp. 62-67.*
Allen et al., "Purification and characterization of a solublepolyurethane degrading enzyme from Comamonasacidovorans", International biodeterioration & biodegradation, vol. 43, 1999, pp. 37-41.
Blake et al., "Adherence and growth of a *Bacillus* species on an insoluble polyester polyurethane", International biodeterioration & biodegradation, vol. 42, 1998, pp. 63-73.
Boubendir, A.: "Purification and Biochemical Evaluation of Polyurethane Degrading Enzymes of Fungal Origin (fungal Enzymes, Ethyl Carbamate, Salicylanilide, Microfungi)" ProQuest Dissertations & Theses Global : The Sciences and Engineering Collection. Dec. 31, 1992 (Dec. 31, 1992), XP002795784.
Crabbe et al., "Biodegradation of a colloidal ester-based polyurethane by soil fungi", International biodeterioration & biodegradation, vol. 33, 1994, pp. 103-113.
Darby et al., "Fungal Susceptibility of Polyurethanes", Applied microbiology, vol. 16, 1968, pp. 900-905.
Database UniProt [Online] "Abhydrolase_3 domain-containing protein", gefunden im EBI accession No. UniProt:G3CRG3 Database accession No. G3CRG3, Nov. 16, 2011.
Database UniProt [Online] Mar. 15, 2017 (Mar. 15, 2017), "Amidase domain-containing protein from Bacillaceae", XP002795786.
Database UniProt [Online] Nov. 16, 2011 (Nov. 16, 2011), "Abhydrolase 3 domain-containing protein", XP002795785.
Database UniProt [Online]Nov. 22, 2017 (Nov. 22, 2017), "Acetyl esterase/lipase aus Planifilum fulgidum", XP002786401.
Hasan et al., "Industrial applications of microbial lipases", Enzyme and Microbial Technology, vol. 39, Issue 2, 2006, pp. 235-251.
Howard et al., "Growth of Acinetobacter gerneri P7 on polyurethane and the purification and characterization of a polyurethanase enzyme", Biodegradation, vol. 23, 2012, pp. 561-573.
International Preliminary Report on Patentability received for PCT Patent Application No. PCT/EP2019/065947, mailed on Dec. 30, 2020, 15 pages (8 pages of English Translation and 7 pages of Original Document).
International Search Report and Written Opinion received for PCT Patent Application No. PCT/EP2019/065947, mailed on Dec. 13, 2019, 21 pages. (10 pages of English Translation and 11 pages of Original Document).

(Continued)

*Primary Examiner* — Robert B Mondesi
*Assistant Examiner* — Mohammad Y Meah
(74) *Attorney, Agent, or Firm* — The Webb Law Firm

(57) ABSTRACT

The present invention relates to new urethanases for the enzymatic breakdown of polyurethanes and to an enzymatic process for the complete breakdown of polyurethanes into defined monomers.

12 Claims, 1 Drawing Sheet

Specification includes a Sequence Listing.

(56) References Cited

OTHER PUBLICATIONS

Jaeger et al., "Microbial lipases form versatile tools for biotechnology", Trends in biotechnology, vol. 16, Issue 9, 1998, pp. 396-403.
Kaplan et al., "Microbial deterioration of polyurethane systems", Dev Ind Microbiol, vol. 82, 1968, pp. 362-371.
Kay et al., "Bacterial degradation of polyester polyurethane", International biodeterioration, vol. 27, 1991, pp. 205-222.
Magnin et al., "Enzymatic recycling of thermoplastic polyurethanes: Synergistic effect of an esterase and an amidase and recovery of building blocks", Waste Management, vol. 85, 2019, pp. 141-150.
Marten et al., "Studies on the enzymatic hydrolysis of polyesters I. Low molecular mass model esters and aliphatic polyesters", Polymer degradation and stability, vol. 80, Issue 3, 2003, pp. 485-501.
Marten et al., "Studies on the enzymatic hydrolysis of polyesters. II. Aliphatic-aromatic copolyesters", Polymer degradation and stability, vol. 88, 2005, pp. 371-381.
Nakajima-Kambe T et al: "Microbial degradation of polyurethane, polyester polyurethanes and polyether polyurethanes", Applied Microbiology and Biotechnology, Springer, DE, vol. 51, No. 2, Feb. 1, 1999 (Feb. 1, 1999), pp. 134-140.
Tang et al., "Enzyme induced biodegradation of polycarbonate-polyurethanes: dose dependence effect of cholesterol esterase", Biomaterials, vol. 24, Issue 12, 2003, pp. 2003-2011.
Vega et al., "Cloning and expression in *Escherichia coli* of apolyurethane-degrading enzyme from Pseudomonasfluorescens", International biodeterioration & biodegradation, vol. 43, 1999, pp. 49-55.
Yukie Akutsu-Shigeno et al: "Isolation of a bacterium that degrades urethane compounds and characterization of its urethane hydrolase", Applied Microbiology and Biotechnology, Springer, Berlin, DE, vol. 70, No. 4, Apr. 1, 2006 (Apr. 1, 2006), pp. 422-429.
Schmidt et al., "Degradation of Polyester Polyurethane by Bacterial Polyester Hydrolases", Polymers 2017, 9, 65; doi:10.3390/polym9020065.
Howard, Chapter 14, Polyurethane Biodegradation, Microbial Degradation of Xenobiotics, Environmental Science and Engineering, Singh (ed.), 2012, pp. 371-394.
NCBI Accession XP OJF 16681.1, Nov. 21, 2016.

\* cited by examiner

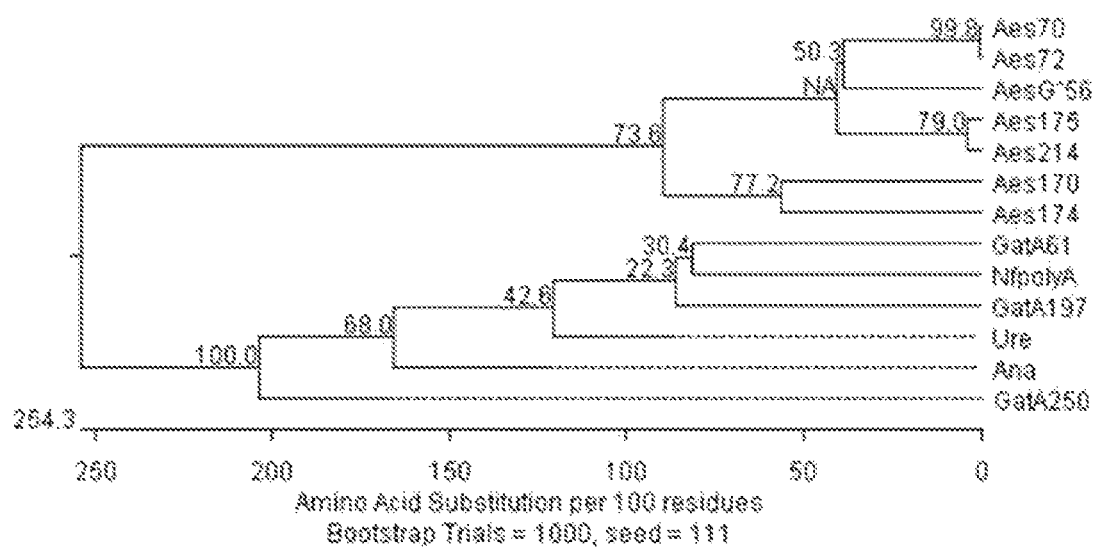

URETHANASES FOR THE ENZYMATIC DEGRADATION OF POLYURETHANES

CROSS-REFERENCE TO RELATED APPLICATIONS

This application is a division of U.S. application Ser. No. 17/254,701, filed Dec. 21, 2020, which is a national stage application (under 35 U.S.C. § 371) of PCT/EP2019/065947, filed Jun. 18, 2019, which claims benefit of European Application No. 18179032.0, filed Jun. 21, 2018, all of which are incorporated herein by reference in their entirety.

REFERENCE TO A SEQUENCE LISTING

The Sequence Listing associated with this application is filed in electronic format via EFS-Web and hereby incorporated by reference into the specification in its entirety. The name of the text file containing the Sequence Listing is 520895.000003_Sequence_Listing. The size of the text file is 38000 bytes, and the text file was created on Mar. 11, 2022.

The present invention relates to new urethanases for the enzymatic breakdown of polyurethanes and to an enzymatic process for the complete breakdown of polyurethanes into defined monomers.

Polyurethanes are established in many areas of normal life. They can be found, for example, in soft foams (mattresses, sponges, upholstered furniture), hard foams (insulation materials, building materials), thermoplastics (sports shoes) or coatings (varnishes, paints, adhesives). The constantly increasing demand for products means that ever greater volumes are being produced. At the same time, there is a growing need for methods that maximize the sustainable recycling of polyurethane products that are no longer needed and so allow the building blocks of the polymers to be reused. For this, the bonds in the polyurethanes must be selectively cleaved in order to be able to obtain defined breakdown products, thereby making them recyclable.

In addition to the physiological functions that enzymes perform in living organisms, enzymes can be used in a diversity of ways for the catalysis of chemical reactions outside this context. Such reactions can be carried out under milder conditions than conventional chemical processes, for example lower temperature, neutral pH, and without the use of aggressive chemicals. Through this it is possible to save on energy, minimize the formation of by-products, and protect the environment, which helps to reduce operating costs. In some cases, it is only through the use of enzymes that it is possible for labile starting materials to be used as reaction feedstocks (Jaeger, K.-E. & Reetz, M. T. (1998) Microbial lipases form versatile tools for biotechnology. Trends in biotechnology, 16, 396-403). Moreover, enzymes are often regio-, stereo- and enantioselective, which makes the purification of the products substantially easier, which can permit the efficient synthesis of products that are otherwise difficult to obtain (Hasan, F., Shah, A. A. & Hameed, A. (2006) Industrial applications of microbial lipases. Enzyme and Microbial Technology, 39, 235-251).

The recycling of polyurethanes is primarily carried out through thermal recycling. This process generally takes place at very high temperatures and with very long reaction times in a batch process, as well as involving the use of catalysts. What can happen in such processes is that thermal breakdown of the polymer chains in cracking reactions leads to undesired and undefined breakdown products or else the formation of epoxy rings occurs, which results in a high odor nuisance and disadvantageous crosslinking of the chains in the recycled raw material, which can make it impossible to reuse said materials in products in particular with close human contact, particularly in the production of foams for use in furniture and mattresses. An alternative option is for complete combustion and thus energy recovery to be carried out, which generates energy, but does not allow efficient reuse of the polymer building blocks.

It is known that polyurethanes can be broken down to a certain degree by bacteria and fungi. Polyester polyurethanes are considerably more susceptible to such microbial/enzymatic breakdown than polyether polyurethanes (Nakajima-Kambe, T., Shigeno-Akutsu, Y., Nomura, N., Onuma, F. & Nakahara, T. (1999) Microbial degradation of polyurethane, polyester polyurethanes and polyether polyurethanes. Applied microbiology and biotechnology, 51, 134-140).

The breakdown of polyester polyurethanes can be readily accomplished by hydrolysis of the ester linkages. The relatively simple breakdown of polyesters is not surprising, given that ester linkages in hydrophobic substrates in nature must also be cleaved when lipids are broken down and polyesters without urethane linkages can likewise be broken down relatively easily by esterases and lipases (Marten, E., Muller, R.-J. & Deckwer, W.-D. (2003) Studies on the enzymatic hydrolysis of polyesters I. Low molecular mass model esters and aliphatic polyesters. Polymer degradation and stability, 80, 485-501; Marten, E., Muller, R.-J. & Deckwer, W.-D. (2005) Studies on the enzymatic hydrolysis of polyesters. II. Aliphatic-aromatic copolyesters. Polymer degradation and stability, 88, 371-381.). Enzymes used to break down polyurethane have been characterized as esterases in various literature sources (Allen, A. B., Hilliard, N. P. & Howard, G. T. (1999) Purification and characterization of a soluble polyurethane degrading enzyme from Comamonas acidovorans. International biodeterioration & biodegradation, 43, 37-41; Blake, R., Norton, W. & Howard, G. (1998) Adherence and growth of a Bacillus species on an insoluble polyester polyurethane. International biodeterioration & biodegradation, 42, 63-73; Crabbe, J. R., Campbell, J. R., Thompson, L., Walz, S. L. & Schultz, W. W. (1994) Biodegradation of a colloidal ester-based polyurethane by soil fungi. International biodeterioration & biodegradation, 33, 103-113; Darby, R. T. & Kaplan, A. M. (1968) Fungal susceptibility of polyurethanes. Applied microbiology, 16, 900-905; Howard, G. T., Norton, W. N. & Burks, T. (2012) Growth of Acinetobacter gerneri P7 on polyurethane and the purification and characterization of a polyurethanase enzyme. Biodegradation, 23, 561-573; Kaplan, A. M., Darby, R. T., Greenberger, M. & Rodgers, M. (1968) Microbial deterioration of polyurethane systems. Dev Ind Microbiol, 82, 362-371; Kay, M., Morton, L. & Prince, E. (1991) Bacterial degradation of polyester polyurethane. International biodeterioration, 27, 205-222; Vega, R. E., Main, T. & Howard, G. T. (1999) Cloning and expression in *Escherichia coli* of a polyurethane-degrading enzyme from Pseudomonas fluorescens. International biodeterioration & biodegradation, 43, 49-55). There is no clear demonstration therein of cleavage of the urethane linkage, since there were no instances of enzyme characterization being carried out on the basis of cleavage of a molecule having a urethane group.

The breakdown of poly(ester urethane)s with fungi or bacteria is described in many publications and patents. However, the breakdown mostly targets only the relatively easily cleaved ester linkages and is mostly demonstrated only by macroscopic observation of polymer breakdown. There is no controlled breakdown here of ester and urethane linkages as in the present invention, and long breakdown times often result. These publications show that urethanases are commonly found enzymes, but provide no demonstration of the specific capabilities, potential uses, and grouping thereof, as employed in the present invention. (JP09192633, Tang, Y. W., Labow, R. S., Santerre, J. P. (2003) Enzyme induced biodegradation of polycarbonate-polyurethanes: dose dependence effect of cholesterol esterase. Biomaterials 24 (12), 2003-2011, Vega, R. E., Main, T. & Howard, G. T. (1999) Cloning and expression in Escherichia coli of a polyurethane-degrading enzyme from Pseudomonas fluorescens. International biodeterioration & biodegradation, 43, 49-55)

A breakdown process for the enzymatic breakdown of poly(ester urethane)s is known, the first step of which is to obtain an esterase from a culture of Comamonas acidovorans strains by using only poly(ester urethane) as the carbon source. In a complicated purification step, the esterase is separated and used for the breakdown of poly (ester urethane)s in a batch process. This gives rise to long breakdown times in a multistage process and no demonstration of specific cleavage of the urethane linkages (JP 09201192, JP 10271994).

The breakdown of poly(ester urethane)s with cutinases, esterases, and/or lipases is described in various patents and publications. However, the breakdown here targets only the relatively simple cleavage of the ester linkages, but not specifically the urethane linkages. In addition, no specific combination of enzymes that cleave ester and urethane linkages is described for the selective control of the breakdown. It can be assumed that the described processes result in little or no cleavage of the urethane linkage. This means that diamines used cannot be recovered efficiently (EP 0968300, U.S. Pat. No. 6,180,381).

WO 2013/134801 describes the breakdown of aromatic polyurethanes based on polyether polyols using an enzyme of class EC 3. No specific enzyme sequences are stated, consequently neither the specificity of the process in the breakdown of particular urethane linkages, nor the controlled cleavage of ester linkages and separate cleavage of urethane linkages, as shown in the present invention, are demonstrated in the cited patent. Moreover, there is no description of the regulation of the pH of the mixture during polymer breakdown in order to maintain urethanase activity. Moreover, no regioselective breakdown is described, nor breakdown of aliphatic poly(ester urethane)s.

WO 2006/019095 describes a urethanase and variants of this enzyme obtained by protein engineering. The enzyme can cleave urethane oligomers based on TDA or MDA. However, bonds are not cleaved regioselectively here, neither is there any application in combination with esterases for the breakdown of polymers. Furthermore, no other urethanases from the GatA or Aes families or any other group are described.

It was thus an object of the present invention to provide further enzymes that can be used for the enzymatic cleavage of urethane linkages and preferably for the complete enzymatic breakdown of polyurethanes. Furthermore, an enzymatic process should be provided that allows the breakdown of polyurethanes into defined monomers.

This object is achieved by the embodiments disclosed in the claims and in the description below.

In a first embodiment, the present invention relates to a polypeptide having an amino acid sequence selected from the group consisting of SEQ ID No. 3, SEQ ID No. 2, SEQ ID No. 4, SEQ ID No. 5, SEQ ID No. 6, SEQ ID No. 8, SEQ ID No. 10 and variants of said polypeptides or to a polypeptide having an amino acid sequence in accordance with SEQ ID No. 7 or a variant thereof, characterized in that the polypeptide has urethanase activity.

Reference for the polypeptides mentioned

| SEQ ID No. | Internal designation | Designation in study |
|---|---|---|
| 1 | Enz01 | GatA61 |
| 2 | Enz02 | Aes70 |
| 3 | Enz03 | Aes72 |
| 4 | Enz04 | Aes170 |
| 5 | Enz05 | Aes174 |
| 6 | Enz06 | Aes175 |
| 7 | Enz07 | GatA197 |
| 8 | Enz08 | Aes214 |
| 9 | Enz09 | GatA250 |
| 10 | Enz10 | AesGö56 |
| 11 | Ref01 | SB12 |
| 12 | Ref02 | SB23 |

Polypeptide

The term "polypeptide" is well known to those skilled in the art. It refers to a chain of at least 50, preferably at least 70, amino acids linked to one another by peptide linkages. A polypeptide may comprise both naturally occurring and synthetic amino acids. It preferably comprises the known proteinogenic amino acids.

For SEQ ID Nos. 1 to 5, 9, and 10, a variant is obtained by adding, deleting or exchanging up to 10%, preferably up to 5%, of the amino acids present in the respective polypeptide. A preferred variant of SEQ ID No. 7 is obtained by adding, deleting or exchanging up to 5% of the amino acids defined in SEQ ID No. 7. Particularly preferred variants of the abovementioned polypeptides are obtained by adding, deleting or exchanging up to 20, preferably up to 10, and more preferably up to 5, amino acids of the disclosed sequences. Preferred variants of SEQ ID No. 6 and SEQ ID No. 8 are obtained by adding, deleting or exchanging up to 3, more preferably up to 2, amino acids. The abovementioned modifications may in principle be executed continuously or discontinuously at any desired point in the polypeptide. However, they are preferably executed only at the N-terminus and/or at the C-terminus of the polypeptide. Each variant obtained by adding, exchanging or deleting amino acids according to the invention is, however, characterized by urethanase activity as defined in this application hereinbelow.

The polypeptides as defined by SEQ ID No. 3, SEQ ID No. 2, SEQ ID No. 4, SEQ ID No. 5, SEQ ID No. 6, SEQ ID No. 8, and SEQ ID No. 10. form a group that is phylogenetically different from the sole enzyme having urethanase activity that is known to date, Ure (see FIG. 1). No enzymes having corresponding activity were previously known from this group. This group of polypeptides is also referred to hereinbelow as "Aes-like".

Urethanase Activity

The term "urethanase activity" refers to the ability of a polypeptide to enzymatically catalyze the cleavage of a urethane group. In this process, each mole of urethane group gives rise to one mole of amine, one mole of alcohol, and one mole of $CO_2$.

The urethane group may be an aromatically or aliphatically attached urethane group. In the case of an aromatically attached urethane group, the nitrogen atom is attached directly to an aromatic ring. In the case of an aliphatically attached urethane group, the nitrogen atom is attached to an alkyl radical. The alkyl radical is preferably unbranched and composed of at least one, more preferably at least two, and most preferably at least three, carbon atoms. In a preferred embodiment of the present invention, the polypeptide having urethanase activity is capable of enzymatically cleaving an aromatically attached urethane group.

Whether a polypeptide has urethanase activity can be checked through the cleavage of suitable model substrates.

The model substrate for the ability to cleave aromatically attached urethane groups is preferably ethyl 4-nitrophenyl carbamate (ENPC). Cleavage is demonstrated by determining the increase in the concentration of 4-nitroaniline. This is done preferably photometrically at a wavelength of 405 nm. The enzyme activity is determined preferably in a reaction buffer containing 100 mM of $K_2HPO_4/KH_2PO_4$, pH 7 with 6.25% by volume of ethanol in the presence of 0.2 mg/L of ENPC as substrate. Incubation of the enzyme with ENPC in the reaction buffer is carried out preferably at room temperature and preferably for 24 hours.

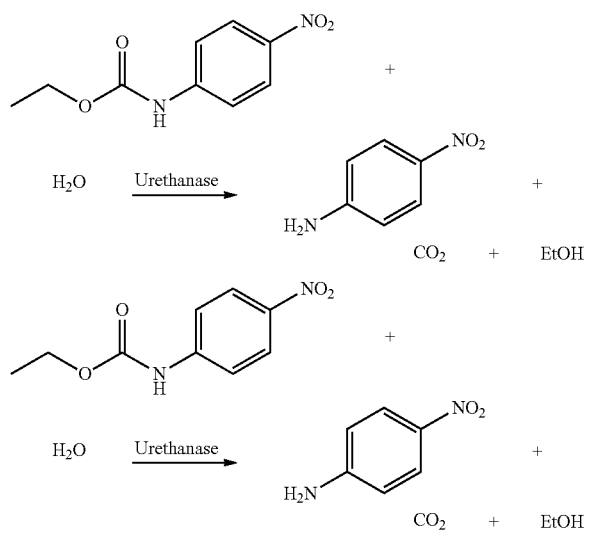

The model substrate for the ability to cleave aliphatically attached urethane groups is preferably ethyl phenethyl carbamate (EPEC). Cleavage is demonstrated by determining the increase in the concentration of phenethylamine. This is done preferably by HPLC. The reaction buffer used and the reaction conditions preferably correspond to the parameters described above for ENPC.

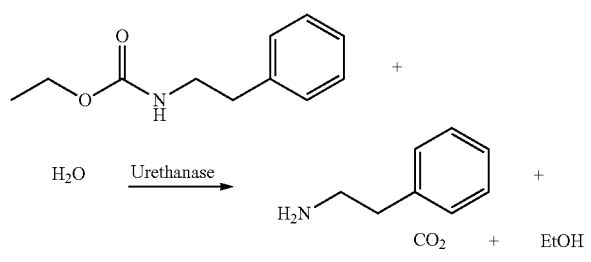

Enzymatic Cleavage

The term "enzymatic cleavage of a urethane group" indicates that the cleavage of a urethane group described above proceeds more rapidly in the presence of a polypeptide having urethanase activity than it does when incubated with the reaction buffer without enzyme under the same reaction conditions or when incubated with the reaction buffer under the same conditions in the presence of an inactive polypeptide. The preferred model for an inactive polypeptide is bovine serum albumin. If, in the presence of a polypeptide being tested, the cleavage of the urethane group proceeds more rapidly than in an otherwise identical control with BSA, said polypeptide possesses urethanase activity as understood in this application.

Use

In a further embodiment, the present invention relates to the use of a polypeptide having an amino acid sequence selected from the group consisting of SEQ ID No. 3, SEQ ID No. 2, SEQ ID No. 4, SEQ ID No. 5, SEQ ID No. 6, SEQ ID No. 8, SEQ ID No. 10 and variants of said polypeptides or to a GatA-similar polypeptide having an amino acid sequence in accordance with SEQ ID No. 7 or a variant thereof, characterized in that the polypeptide has urethanase activity in the enzymatic cleavage of urethane linkages.

Unless explicitly defined otherwise, all definitions given above apply to this embodiment too.

Breakdown of Urethanes into Low-Molecular-Weight Breakdown Products

In a further embodiment, the present invention relates to a process for breaking down polyester polyurethanes into low-molecular-weight breakdown products, comprising the steps of
a) cleaving the ester groups present in the polyester polyurethane; and
b) cleaving the urethane groups present in the polyester polyurethane with a polypeptide that has urethanase activity;
with the proviso that process steps a) and b) may be carried out in either order or else in parallel.

Particularly suitable as peptides having urethanase activity are the peptides described in this application having amino acid sequences as defined in the group consisting of SEQ ID Nos. 1, 2, 3, 4, 5, 6, 7, 8, 9, and 10 and amino acid sequences having at least 90% sequence identity with the abovementioned sequences. Very particular preference is given to peptides having amino acid sequences as defined in SEQ ID No. 3 or 7 and amino acid sequences having at least 90% sequence identity with the abovementioned sequences.

Consequently, in a particularly preferred embodiment, the present invention relates to a process for breaking down polyester polyurethanes into low-molecular-weight breakdown products, comprising the steps of
a) cleaving the ester groups present in the polyester polyurethane; and
b) treating the polyurethane with a polypeptide that has urethanase activity and has an amino acid sequence selected from the group consisting of SEQ ID No. 1 to SEQ ID No. 10 and amino acid sequences having at least 90% sequence identity with the abovementioned sequences;
with the proviso that process steps a) and b) may be carried out in either order or else in parallel.

Preference is given to carrying out process step a) before process step b).

Process step a) is preferably carried out with a lipase. This lipase is preferably water-soluble and not present in an immobilized form. "Immobilized" here refers to the attachment of peptides that is generally known in biotechnology, particularly the attachment of antibodies or enzymes, to the surface of vessels or to water-insoluble particles.

Particular preference is given to using a lipase capable of cleaving tributyrin. Even more particular preference is given to using a polypeptide that has an amino acid sequence as defined in SEQ ID No. 11 or SEQ ID No. 12 or that has an amino acid sequence having at least 90%, preferably at least 95%, sequence identity with one of the two abovementioned sequences and which is capable of cleaving tributyrin. Process step a) is preferably carried out under reaction conditions in which the employed lipase shows activity. Such conditions can be determined by routine experiments using common biochemical methods.

Since the polypeptides having urethanase activity according to the invention have their maximum activity in the neutral range, process step b) is preferably carried out at a pH between 6.0 and 10.0, preferably between 6.0 and 8.0. The pH may be adjusted using all suitable bases known to those skilled in the art.

The term "polyester polyurethane" refers to a polyurethane formed from one or more polyester polyols and one or more isocyanates. The polyurethane may be foamed or non-foamed. It is preferably foamed. To increase the specific surface area, it is preferable to comminute the polyurethane before carrying out process steps a) and b). This is particularly preferable when polyurethane is to be used in non-foamed form. Comminution may be done in any way familiar to those skilled in the art, preferably by milling, slicing, tearing or cutting.

The polyurethane comprises as the isocyanate component at least one aromatic, aliphatic or cycloaliphatic isocyanate. The polyurethane preferably comprises only aromatic isocyanates. Preferred aromatic isocyanates are methylene diphenyl isocyanate (MDI), MDI variants having three or more aromatic rings, naphthylene diisocyanate, and tolylene diisocyanate. Particularly preferred aromatic isocyanates are methylene diphenyl isocyanate (MDI), MDI variants having three or more aromatic rings, and tolylene diisocyanate. MDI variants having three or more aromatic rings are synthesis by-products and may also be present in polyurethanes. The polyurethane to be broken down particularly preferably comprises tolylene 2,4-diisocyanate and tolylene 2,6-diisocyanate.

The term "polyester polyol" is known to those skilled in the art and describes polyesters containing an average of at least 1.5, preferably at least 1.8, and more preferably at least 2.0, hydroxyl groups per molecule. The polyester polyols present in the polyurethane to be broken down particularly preferably have functionality of between 1.5 and 6.0. They contain as structural elements aromatic and/or aliphatic polyols and also aromatic and/or aliphatic polycarboxylic acids in any combination.

The low-molecular-weight breakdown products of the polyester-based polyurethane foams preferably have a molecular weight of not more than 1000 g/mol. These are preferably
(i) amines derived from the isocyanates used in the production of the polyurethane concerned, for example tolylene-2,4-diamine in the case of tolylene 2,4-diisocyanate; and
(ii) alcohols and carboxylic acids used to form the polyester polyols employed in the synthesis of the polyurethane concerned.

A "polyol" is in this application understood as meaning any compound having at least two hydroxyl groups. Said polyol preferably has a molecular weight of not more than 300 g/mol. Preferred polyols that are low-molecular-weight breakdown products of polyester-based polyurethane foams are selected from the group consisting of ethylene glycol, diethylene glycol, 1,4-butanediol, triethylene glycol, propylene glycol, 1,2-dipropylene glycol, neopentyl glycol, glycerol, 1,1,1-trimethylolpropane, sucrose, sorbitol, and pentaerythritol.

A "polycarboxylic acid" is in this application understood as meaning any compound containing at least two carboxyl groups. Said polycarboxylic acid preferably has a molecular weight of not more than 300 g/mol. Preferred polycarboxylic acids that are low-molecular-weight breakdown products of polyester-based polyurethane foams are selected from the group consisting of succinic acid, glutaric acid, adipic acid, phthalic acid, terephthalic acid, benzenetricarboxylic acid, oleic acid, and ricinoleic acid. Particularly preferred polycarboxylic acids that are low-molecular-weight breakdown products of polyester-based polyurethane foams are selected from the group consisting of succinic acid, glutaric acid, adipic acid, phthalic acid, terephthalic acid, and benzenetricarboxylic acid.

A "polyamine" is in this application understood as meaning any compound containing at least two amino groups. Said polyamine preferably has a molecular weight of not more than 300 g/mol. Preferred polyamines that are low-molecular-weight breakdown products of the polyester-based polyurethane foams are selected from the group consisting of methylene-4,4'-diamine, methylene-2,4'-diamine, methylene-2,2'-diamine, tolylene-2,4-diamine, tolylene-2,6-diamine, hexamethylenediamine, isophorone diamine, xylylenediamine, pentamethylenediamine, para-phenylenediamine, butyldiamine, and H12-methylenediamine. Further preference is given to polyamines selected from the group consisting of methylene-4,4'-diamine, methylene-2,4'-diamine, methylene-2,2'-diamine, naphthylene-1,4-diamine, naphthylene-1,5-diamine, naphthylene-1,6-diamine, tolylene-2,4-diamine, and tolylene-2,6-diamine. Particular preference is given to polyamines selected from the group consisting of methylene-4,4'-diamine, methylene-2,4'-diamine, methylene-2,2'-diamine, tolylene-2,4-diamine, and tolylene-2,6-diamine.

The process according to the invention allows effective recycling of polyurethanes in two ways: (i) The process itself operates under mild reaction conditions and so does not require a high input of energy and (ii) it allows the polyurethane to be recycled, because defined breakdown products are formed that are themselves valuable chemical raw materials.

By comparison, thermal glycolysis, which is currently the most common chemolysis for recycling polyurethane and has already been put into practice industrially, is carried out at very high temperatures. The focus here is on extraction of the polyols, whereas the amines are separated as an interfering species and are not recovered. In non-enzymatic hydrolysis, both polyols and amines are obtained as products. However, this process is carried out at high temperatures and high ambient pressures.

OVERVIEW OF THE FIGURES

FIG. 1: Result of the phylogenetic analysis of the amino acid sequences disclosed in the present application The working examples that follow serve merely to elucidate the invention. They are not intended to limit the scope of the claims in any way.

EXAMPLES

Test of Enzyme Activity with ENPC 0.2 mg/ml of ENPC was incubated for 24 hours in 100 mM $KH_2PO_4/K_2HPO_4$ at pH 7.0 containing 6.25% by volume of ethanol at room temperature and 900 rpm on the "MTS 2/4" plate shaker (IKA, Staufen).

After filtering the samples, 100 μL of each was transferred to transparent flat-bottom 96-well "UV-Star" plates (Greiner Bio-One, Frickenhausen) and the absorbance at 405 and 480 nm determined. The value at 480 nm was measured, because 4-nitroaniline does not show any significant absorption and, if high values are observed at both wavelengths, it is highly likely that is not 4-nitroaniline but another substance that was responsible for the absorbance at 405 nm.

Hydrolysis by urethanases causes cleavage of the almost colorless ENPC into 4-nitroaniline, $CO_2$, and ethanol, resulting in the detection of 4-nitroaniline at 405 nm in the "Infinite M1000PRO" microtiter plate photometer (Tecan, Mannedorf, Switzerland). The photometer was controlled using the "i-control" software (Tecan, Mannedorf, Switzerland), version 3.4.2.0. 4-Nitroaniline was additionally detected by HPLC using the "dabsylamine" method.

High Pressure Liquid Chromatography (HPLC)

High-pressure liquid chromatography was carried out on an Agilent Technologies (Santa Clara, USA) 1100 series instrument equipped with an autosampler and DAD (diode array detector) for UV and the visible light region. All measurements were carried out using a "Zorbax XDB-C18" column having a particle size of 3.5 μm and dimensions of 4.6×75 mm (Agilent Technologies, Santa Clara, USA). In all methods, a 5 μL sample was injected into a column heated to 40° C. The flow was generally 1.5 ml/min. The use of a reverse-phase column means that elution in all methods is with increasing concentrations of organic solvent.

Detection and quantification of dabsylated aliphatic amines and urethanes was done using the "dabsylamine" method. This method allows the quantification of aromatic amines and urethanes without derivatization on account of their high intrinsic absorption. Also used as eluent in addition to AcN was 10 mM sodium phosphate buffer pH 7.0, to which 0.005% (w/v) sodium azide was added to protect against microbial growth. In order to prevent pressure problems caused by contaminated pump valves, 5% (v/v) of dd $H_2O$ was later added to the AcN and the method adjusted ("Dabsylamin95"). The MDEC formed from the enzyme-catalyzed reactions of 4,4'-MDA with EC was quantified using the "Dabsylamin-12-MeOH" method, in which the aqueous component is acidified and the protonated aromatic amines thereby generated elute very early. The reactions of 4,4'-MDA with DMC, 2,4-TDA with DMC, and 2,4-TDA with EC were investigated using the "Dabsylamin95-H2O" method, which differs from "Dabsylamin95" only in that pure dd $H_2O$ is used instead of buffer. The data were analyzed using the "OpenLAB CDS ChemStationLC" software, version A.02.09 [017] (Agilent Technologies, Santa Clara, USA).

Dabsylamine: Eluent: AcN and 10 mM $Na_2HPO_4/NaH_2PO_4$, pH 7.0

| t [min] | AcN |
| --- | --- |
| 0 | 5 |
| 6.5 | 85 |
| 8.0 | 5 |
| 10.0 | 5 |

Dabsylamin95: Eluent: AcN containing 5% (v/v) dd $H_2O$ and 10 mM $Na_2HPO_4/NaH_2PO_4$, pH 7.0

| t [min] | % AcN (+5% (v/v) dd $H_2O$) |
| --- | --- |
| 0 | 5 |
| 6.5 | 90 |
| 8.0 | 5 |
| 10.0 | 5 |

Dabsylannin-12-MeOH-lang: Eluent: Methanol and dd $H_2O$ containing 0.1% (v/v) methanoic acid

| t [min] | % methanol |
| --- | --- |
| 0 | 5 |
| 2.5 | 35 |
| 8.0 | 70 |
| 8.5 | 85 |
| 10.0 | 5 |
| 12.0 | 5 |

| SEQ ID No. | Designation in study | Hydrolysis of ENPC |
| --- | --- | --- |
| 1 | GatA61 | + |
| 2 | Aes70 | + |
| 3 | Aes72 | + |
| 4 | Aes170 | + |
| 5 | Aes174 | + |
| 6 | Aes175 | + |
| 7 | GatA197 | + |
| 8 | Aes214 | + |
| 9 | GatA250 | + |
| 10 | AesGö56 | + |
| 11 | SB12 | + |
| 12 | SB23 | + |

Test of Enzyme Activity with EPEC

The test was carried out as described for ENPC. The phenethylamine formed was detected by HPLC as described above.

| SEQ ID No. | Designation in study | Hydrolysis of EPEC |
| --- | --- | --- |
| 1 | GatA61 | + |
| 2 | Aes70 | − |
| 3 | Aes72 | + |
| 4 | Aes170 | − |
| 5 | Aes174 | + |
| 6 | Aes175 | − |
| 7 | GatA197 | + |
| 8 | Aes214 | + |
| 9 | GatA250 | + |
| 10 | AesGö56 | − |
| 11 | SB12 | + |
| 12 | SB23 | + |

Phylogenetic Analysis of the Enzymes

Phylogenetic trees showing the relatedness of the urethanases were created using the "MegAlign" software (DNASTAR, Madison, USA), version 10.1.0. The phylogenetic trees were created with the default settings using "ClustalW".

Alignments of the different proteins were created using the "Clustal Omega" software (Sievers et al., 2011).

Database searches for protein sequences were carried out using BLASTP (Altschul et al., 1990).

Open reading frames (ORFs) in sequenced metagenome sequences were located using the online application "ORF Finder" from the NCBI (Wheeler et al., 2007).

Identical hydrolase genes were reduced to a single representative and all sequences examined with ORFs in order to obtain the complete sequences of the genes. Alternative start codons were also allowed in the search. It was evident here that the gene from pLip214 included an N-terminal region with similarity to aes, but without a start codon having been identified. This gene segment was not located on the edge of the insert of the metagenome vector, which could explain a truncated gene. For further analyses, the region with similarity to aes but without a start codon was used as the sequence for this gene. The identified putative urethanase genes were translated in silico and compared with the NCBI database using BLASTP. The putative urethanases were named on the basis of their number in the lipase bank and the similarity to GatA or Aes.

In order to compare the individual members of the two identified urethanase groups (GatA and Aes), an alignment was in each case created with the "Clustal Omega" software and a phylogenetic tree additionally created with the "MegAlign" software, with a common alignment of the two groups created for the phylogenetic tree. The sequence comparison also included the sequences for the enzymes from the literature (Ure, Ana, and NfpolyA), which all showed similarity with GatA.

The phylogenetic tree is shown in FIG. 1. This shows that the two groups are located in different branches, the similarities within the two groups being not so clear in some instances, as can be seen from the lower bootstrapping values at the nodes. Within the GatA group there seem to be greater differences than within the Aes group, as can be seen from the longer branch lengths in this group. In particular Aes70 and Aes72 and also Aes175 and Aes214 show very high similarity, as manifested both by the relatively short branches in the phylogenetic tree and by the same protein with greatest similarity having been found in the BLASTP search.

Production of the Polyurethane Foam for the Breakdown Tests

The starting materials listed below were reacted in the manner of processing customary for the production of polyurethane foams in the one-step process.

The bulk density was 38 kg/m³ (DIN EN ISO 845 in the version of October 2009), the compressive strength at 40% compression was 3.5 kPa (DIN EN ISO 3386-1 in the version of October 2015)

Formulation

| | |
|---|---|
| 100 parts | Desmophen 2200B |
| 3 parts | water |
| 19 parts | Desmodur T80 |
| 19 parts | Desmodur T65 |
| 0.7 parts | N,N'-dimethylpiperazine |
| 1 part | Tegostab 8325 |

Raw Materials

Desmophen® 2200B, Covestro Deutschland AG; branched polyester polyol based on adipic acid, diethylene glycol and 1,1,1-trimethylolpropane having a hydroxyl value of approx. 60 mg KOH/g.

Desnnodur® T80, Covestro Deutschland AG; isomer mixture comprising tolylene 2,4- and 2-6-diisocyanate in a mixture ratio of approx. 80:20.

Desnnodur® T65, Covestro Deutschland AG; isomer mixture comprising tolylene 2,4- and 2-6-diisocyanate in a mixture ratio of approx. 67:33.

N,N'-Dimethylpiperazine, catalyst from abcr GmbH

Tegostab®B 8325, foam stabilizer, from Evonik

Water; deionized water

The formulation may be executed with indices of 90 to 115. The index is defined as the molar ratio of isocyanate groups to isocyanate-reactive groups multiplied by 100.

Breakdown of Polyurethane Foam

The substrate used was a polyester polyurethane produced with tolylene diisocyanate. Breakdown took place in two reaction steps. First, the foam was incubated with a lipase. The resulting oligomers were neutralized and then cleaved into monomers with a urethanase.

In the first step, 1 g of the foam was transferred to a 50 ml centrifuge tube with 20 ml of potassium phosphate buffer pH 7.0 and approx. 30 mg of CalB lyophilizate ("Chirazyme L2" from Roche, Basel, Switzerland) (here referred to as SEQ ID No. 12) and incubated at 37° C. and 200 rpm for 5 days. Fragments of the foam residues were photographed with a "MH2" microscope (Olympus, Hamburg) by comparison with a negative control without enzyme. The turbid solution was then centrifuged for 10 minutes at 25° C. and 4000 rpm in a large-capacity centrifuge. The clear supernatant was adjusted to pH 7.0 with 1 M NaOH. After about 6 hours at room temperature, the slight fall in pH was retitrated to 7.0 and the solution underwent a sterilizing filtration. The soluble oligomers were stored at 4° C. until use.

For further use, the soluble oligomers were transferred to 1.5 mL reaction vessels and mixed with 20 µL of DMF and 150 µL of the optimal buffer for the respective urethanase (100 mM sodium phosphate buffer, adjusted to the respective optimal pH for the urethanase in the pH 6.0 to pH 8.0 range). To each was then added 30 µL of the undiluted, purified urethanase and the mixtures were shaken on the heating block at 30° C. and 1000 rpm. A mixture containing enzyme storage buffer was used as the negative control. After three days, the batches were filtered through filter plates with a PVDF membrane and a pore size of 0.2 µm (Corning, Kaiserslautern) and the filtrate was analyzed by HPLC using the "Dabsylamine95" method in respect of the tolylene 2,4- and 2-6-diisocyanate formed.

After the reaction in the mixture containing the CalB lyophilizate, it was already macroscopically evident by comparison with a negative control without enzyme that the foam had lost all structure and was present as a turbid suspension containing small particles of foam. The buffer, which had been almost completely absorbed by the foam at the start of the experiment, subsequently contained the entire foam mass in the form of broken-down particles. HPLC analysis showed clear peaks that were assigned to the oligomers formed, but no peaks pointing to the formation of tolylenediamine (TDA) (data not shown).

The oligomer solution was treated with all of the expressed urethanases and with SEQ ID No. 12 and then examined by HPLC for the formation of TDA. This was demonstrated for the mixtures containing SEQ ID No. 7 and SEQ ID No. 3, with the measured amount of 2,6-TDA being approximately the same in the two mixtures and the formation of 2,4-TDA in the mixture containing Enz03 found to be markedly more pronounced. SEQ ID No. 3 afforded 0.057 g/L of 2,4-TDA and 0.025 g/L of 2,6-TDA, whereas SEQ ID No. 7 resulted in the formation of 0.0075 g/L of 2,4-TDA and 0.024 g/L of 2,6-TDA. In addition, in contrast to the other mixtures, the oligomer peaks for these two enzymes showed changes and a general reduction in size. In the case of SEQ ID No. 7, TDA was cleaved from the polyester PU foam even without prior pretreatment, whereas in the case of SEQ ID No. 3 this was possible only by providing neutralized oligomers after prior ester cleavage. The fact that the product peaks identified as oligomer peaks from the hydrolysis with SEQ ID No. 12 were dramatically smaller after further treatment with urethanases, this being accompanied by significant TDA formation, confirmed that these were oligomer peaks.

It was also demonstrated that insoluble TDI-based polyester-polyurethane foam can be cleaved into its monomers by a combination of two reaction steps. In a first step, the PU foam was predigested using the lipase CalB through hydrolysis of the ester linkages. After neutralization, the liberated oligomers served as a substrate for the overexpressed urethanases. This was accompanied by hydrolysis of the urethane linkages and the detection of TDA in monomeric form.

In conclusion, it can be seen that a combination of hydrolytic cleavage of the ester linkages by means of lipases, neutralization of the oligomer solution, and subsequent hydrolytic cleavage of the urethane linkages permits the complete breakdown of polyurethanes into defined monomers.

The invention claimed is:

1. A method comprising utilizing a polypeptide for cleaving a urethane group, the polypeptide having an amino acid sequence selected from the group consisting of SEQ ID No. 3, SEQ ID No. 2, SEQ ID No. 4, SEQ ID No. 5, SEQ ID No. 6, SEQ ID No. 8, SEQ ID No. 10, SEQ ID No. 7, and variants of said polypeptides, characterized in that the polypeptide has urethanase activity in the enzymatic cleavage of urethane linkages, wherein variants is defined as an amino acid sequence having at least 90% sequence identity with a polypeptide to which it refers.

2. The method according to claim 1, wherein the urethane group is aromatically attached, wherein aromatically attached is defined as a nitrogen atom of the urethane group being directly attached to an aromatic ring.

3. The method according to claim 1, wherein the polypeptide has an amino acid sequence selected from the group consisting of SEQ ID No. 3, SEQ ID No. 2, SEQ ID No. 4, SEQ ID No. 5, SEQ ID No. 6, SEQ ID No. 8, SEQ ID No. 10, SEQ ID No. 7, and variants of said polypeptides, wherein variants is defined as an amino acid sequence having at least 95% sequence identity with a polypeptide to which it refers.

4. The method according to claim 1, wherein the polypeptide has an amino acid sequence selected from the group consisting of SEQ ID No. 3, SEQ ID No. 2, SEQ ID No. 4, SEQ ID No. 5, SEQ ID No. 6, SEQ ID No. 8, SEQ ID No. 10, and SEQ ID No. 7.

5. The method according to claim 1, wherein the polypeptide has an amino acid sequence selected from the group consisting of SEQ ID No. 3, SEQ ID No. 2, SEQ ID No. 4, SEQ ID No. 5, SEQ ID No. 6, SEQ ID No. 8, SEQ ID No. 10.

6. The method according to claim 1, wherein the polypeptide has an amino acid sequence in accordance with SEQ ID No. 7 or a variant thereof.

7. The method according to claim 1, wherein the polypeptide has an amino acid sequence in accordance with SEQ ID No. 2 or a variant thereof.

8. The method according to claim 1, wherein the polypeptide has an amino acid sequence in accordance with SEQ ID No. 3 or a variant thereof.

9. The method according to claim 1, wherein the polypeptide has an amino acid sequence in accordance with SEQ ID No. 4 or a variant thereof.

10. The method according to claim 1, wherein the polypeptide has an amino acid sequence in accordance with SEQ ID No. 5 or a variant thereof.

11. The method according to claim 1, wherein the polypeptide has an amino acid sequence in accordance with SEQ ID No. 6 or a variant thereof.

12. The method according to claim 1, wherein the polypeptide has an amino acid sequence in accordance with SEQ ID No. 8 or a variant thereof.

* * * * *

SEQUENCE LISTING

```
<160> NUMBER OF SEQ ID NOS: 12

<210> SEQ ID NO 1
<211> LENGTH: 469
<212> TYPE: PRT
<213> ORGANISM: Unknown
<220> FEATURE:
<223> OTHER INFORMATION: Derived from metagenome

<400> SEQUENCE: 1

Met Met Gly Gly Val Gly Val Arg Glu Glu Leu Ala Thr Trp Thr Ala
1               5                   10                  15

Val Arg Leu Ala Glu His Ile Arg Lys Lys Glu Leu Ser Pro Val Glu
            20                  25                  30

Val Thr Asp Tyr Phe Leu Arg Arg Ile Glu Ala Leu Asn Pro Ala Val
        35                  40                  45

Asn Ala Phe Cys Thr Val Asp Ala Asp Gly Ala Met Arg Ala Ala Lys
    50                  55                  60

Ala Ala Glu Gln Arg Leu Met Ala Gly Glu Thr Pro Pro Leu Leu Gly
65                  70                  75                  80

Val Pro Val Ala Ile Lys Asp Leu Thr Pro Thr Lys Gly Ile Arg Thr
                85                  90                  95

Thr Tyr Gly Ser Arg Leu Phe Ala Asp Asn Val Pro Glu Ala Asp Ala
            100                 105                 110

Val Leu Val Thr Arg Leu Lys Gln Ala Gly Ala Ile Ile Val Gly Lys
        115                 120                 125

Thr Asn Thr Pro Glu Phe Gly His Ala Gly Val Thr Asp Asn Arg Leu
    130                 135                 140

Phe Gly Arg Thr Asn Asn Pro Trp Asp Leu Ser Arg Ile Ala Gly Gly
145                 150                 155                 160

Ser Ser Gly Gly Ser Asp Gly Gly Ser Ile Arg Ile Pro Ala Ser
                165                 170                 175

Cys Cys Gly Ile Phe Gly Phe Lys Pro Thr Phe Gly Arg Val Pro His
            180                 185                 190

Asp Thr Gly Ala Thr Ala Phe Ser Ile Thr Ala Pro Phe Leu His His
        195                 200                 205
```

```
Gly Pro Met Ser Arg Thr Val Glu Asp Ser Val Leu Met Leu Ala Ala
    210                 215                 220

Met Gln Gly Pro Asp Gly Cys Asp Pro Phe Ser Leu Pro Leu Pro Gly
225                 230                 235                 240

Ile Asp Trp Pro Leu Ser Ala Glu Ile Lys Pro Phe Ser Gln Trp Arg
                245                 250                 255

Ile Ala Tyr Ser Pro Asn Leu Asp Phe Tyr Ala Ile Asp Pro Ala Val
            260                 265                 270

Arg Gln Val Met Glu Gln Ala Val Ser Ala Leu Gln Gly Leu Gly Cys
        275                 280                 285

Arg Val Glu Glu Val Arg Leu Gly Leu Glu Gly Lys Thr Leu Val
    290                 295                 300

Leu Glu Thr Phe Ala Arg Leu Trp Ala Val His Tyr Ala Ala Phe Tyr
305                 310                 315                 320

Glu Glu Leu Leu Glu Arg Glu Ala Glu Leu Ser Lys Gly Phe Val Ala
                325                 330                 335

Thr Ile Arg Tyr Gly Gln Gln Phe Ser Ala Val Glu Tyr Lys Arg Leu
            340                 345                 350

Glu Arg Pro Arg Ala Val Val Tyr Glu Arg Val Glu Asn Val Phe Ala
        355                 360                 365

Lys Tyr Asp Leu Leu Ile Thr Pro Thr Leu Ala Val Pro Pro Phe Ala
    370                 375                 380

His Asp Cys Pro Pro Arg Glu Ile Asp Gly Lys Ala Val Asn Pro Tyr
385                 390                 395                 400

Asn Glu Trp Met Leu Thr Ser Ile Phe Asn Leu Thr Gly His Pro Val
                405                 410                 415

Ala Ser Ile Pro Ala Gly Phe Ser Pro Glu Gly Leu Pro Ile Gly Met
            420                 425                 430

Gln Ile Val Gly Pro Arg Leu Ala Asp Ala Ala Val Leu Glu Phe Ala
        435                 440                 445

Tyr Leu Phe Glu Gln Thr Val Ala Pro Arg Arg Pro Tyr Pro Cys Asp
    450                 455                 460

Asp Val Arg Leu Asn
465

<210> SEQ ID NO 2
<211> LENGTH: 264
<212> TYPE: PRT
<213> ORGANISM: Unknown
<220> FEATURE:
<223> OTHER INFORMATION: Derived from metagenome
<220> FEATURE:
<221> NAME/KEY: misc_feature
<222> LOCATION: (252)..(252)
<223> OTHER INFORMATION: Xaa can be any naturally occurring amino acid

<400> SEQUENCE: 2

Leu Asp Tyr Leu Gly Gly Phe Ser Pro Leu Glu Ser Asp Val Thr Val
1               5                   10                  15

Glu Lys Thr Arg Ile Ala Gly Val Pro Gly Glu Trp Ile Ser Thr Pro
            20                  25                  30

Asp Ala Arg Lys Asp Arg Val Leu Phe Tyr Leu His Gly Gly Ala Tyr
        35                  40                  45

Cys Phe Gly Ser Cys Asp Ser His Arg Gly Leu Val Ser Arg Leu Ala
    50                  55                  60

Arg Ala Cys Gly Ser Arg Ala Leu Leu Ile Glu Tyr Arg Leu Ala Pro
65                  70                  75                  80
```

```
Glu His Pro Phe Pro Ala Ala Leu Glu Asp Ser Thr Ala Ala Tyr Arg
                85                  90                  95

Glu Leu Ile Arg Ser Gly Val Arg Pro Glu Asn Leu Val Ile Ala Gly
            100                 105                 110

Asp Ser Ala Gly Gly Leu Thr Met Ala Thr Leu Leu Thr Leu Arg
        115                 120                 125

Asp Glu Gly Asp Pro Leu Pro Ser Ala Ala Val Leu Leu Ser Pro Trp
130                 135                 140

Thr Asp Leu Glu Gly Thr Gly Glu Ser Met Lys Thr Lys Ala Asp Val
145                 150                 155                 160

Glu Pro Trp Leu Asp Pro Glu Lys Ser His Leu Leu Ala Lys Leu Tyr
                165                 170                 175

Leu Gly Asp Leu Asp Pro Arg His Pro Leu Val Ser Pro Ile His Ala
            180                 185                 190

Asp Leu Asn Asn Leu Pro Pro Leu Val His Val Gly Ser Asp Glu
        195                 200                 205

Cys Leu Leu Asp Asp Ser Val Arg Leu Val Glu Arg Ala Lys Ser Ala
        210                 215                 220

Gly Val Glu Thr Glu Phe Lys Ile Cys Asp Glu Met Trp His Val Phe
225                 230                 235                 240

His Gly Phe Pro Ile Pro Glu Ala Gln Gln Ala Xaa Glu Glu Ile Gly
                245                 250                 255

Ala Phe Val Arg Ala Arg Leu Pro
                260

<210> SEQ ID NO 3
<211> LENGTH: 297
<212> TYPE: PRT
<213> ORGANISM: Unknown
<220> FEATURE:
<223> OTHER INFORMATION: Derived from metagenome

<400> SEQUENCE: 3

Met Ala Ser Pro Gln Ser Glu Ala Ile Arg Gln Met Leu Arg Glu Gln
1               5                   10                  15

Lys Glu Ala Ala Lys Lys Gly Ala Pro Ser Ile Glu Glu Gln Arg Arg
            20                  25                  30

Gln Leu Asp Tyr Leu Gly Gly Phe Ser Pro Leu Glu Ser Asp Val Thr
        35                  40                  45

Val Glu Lys Thr Arg Ile Ala Gly Val Pro Gly Glu Trp Ile Ser Thr
    50                  55                  60

Pro Asp Ala Arg Lys Asp Arg Val Leu Phe Tyr Leu His Gly Gly Ala
65                  70                  75                  80

Tyr Cys Phe Gly Ser Cys Asp Ser His Arg Gly Leu Val Ser Arg Leu
                85                  90                  95

Ala Arg Ala Cys Gly Ser Arg Ala Leu Leu Ile Glu Tyr Arg Leu Ala
            100                 105                 110

Pro Glu His Pro Phe Pro Ala Ala Leu Glu Asp Ser Thr Ala Ala Tyr
        115                 120                 125

Arg Glu Leu Ile Arg Ser Gly Val Arg Pro Glu Asn Leu Val Ile Ala
    130                 135                 140

Gly Asp Ser Ala Gly Gly Gly Leu Thr Met Ala Thr Leu Leu Thr Leu
145                 150                 155                 160

Arg Asp Glu Gly Asp Pro Leu Pro Ser Ala Ala Val Leu Leu Ser Pro
                165                 170                 175
```

Trp Thr Asp Leu Glu Gly Thr Gly Glu Ser Met Lys Thr Lys Ala Asp
            180                 185                 190

Val Glu Pro Trp Leu Asp Pro Glu Lys Ser His Leu Leu Ala Lys Leu
        195                 200                 205

Tyr Leu Gly Asp Leu Asp Pro Arg His Pro Leu Val Ser Pro Ile His
    210                 215                 220

Ala Asp Leu Asn Asn Leu Pro Pro Leu Leu Val His Val Gly Ser Asp
225                 230                 235                 240

Glu Cys Leu Leu Asp Asp Ser Val Arg Leu Val Glu Arg Ala Lys Ser
                245                 250                 255

Ala Gly Val Glu Thr Glu Phe Lys Ile Trp Asp Glu Met Trp His Val
                260                 265                 270

Phe His Gly Phe Pro Ile Pro Glu Ala Gln Gln Ala Ile Glu Glu Ile
            275                 280                 285

Gly Ala Phe Val Arg Ala Arg Leu Pro
    290                 295

<210> SEQ ID NO 4
<211> LENGTH: 311
<212> TYPE: PRT
<213> ORGANISM: Unknown
<220> FEATURE:
<223> OTHER INFORMATION: Derived from metagenome

<400> SEQUENCE: 4

Met Ala Asp Pro Gln Leu Glu Ala Val Leu Val Gly Leu Ala Gln Ala
1               5                   10                  15

Ser Ala Gly Ala Gln Gly Pro Ala Thr Val Glu Gly Phe Arg Val Ala
                20                  25                  30

Leu Arg Glu Leu Thr Arg Met Leu Asp Phe Arg Asp Ile Pro Val Gly
            35                  40                  45

Arg Val Glu Asn Arg Met Ile Pro Gly Pro Asp Gly Glu Ile Gly Ile
50                  55                  60

Arg Ile Tyr Thr Pro Ile Ala Ala Gly Ala Arg Met Leu Glu Thr Leu
65                  70                  75                  80

Ile Tyr Phe His Gly Gly Gly Phe Val Ala Gly Asp Leu Glu Thr His
                85                  90                  95

Asp Thr Leu Cys Arg Gly Leu Thr Ala Arg Ser Gly Cys Arg Val Ile
            100                 105                 110

Ser Val Asp Tyr Arg Leu Ala Pro Glu His Pro Phe Pro Ala Ala Ile
        115                 120                 125

Asp Asp Ser Tyr Ala Ala Leu Arg Trp Ile Glu Ala Asn Ala Thr Thr
130                 135                 140

Leu Gly Val Asp Ser Asn Arg Ile Ala Val Gly Gly Asp Ser Ala Gly
145                 150                 155                 160

Gly Asn Ile Ala Ala Val Val Ala Gln Leu Ala Arg Gly Ala Gly Asn
                165                 170                 175

Pro Val Val Arg Phe Gln Leu Leu Ile Tyr Pro Val Val Gln Trp Asp
            180                 185                 190

Val Ala Thr Pro Ser Arg Gln Gln Phe Ala Glu Asp Pro Ile Ile Pro
        195                 200                 205

Arg Asp Val Ile Asp Met Cys Ala Arg Asn Tyr Phe Gly Pro Met Val
    210                 215                 220

Pro Ala Thr Asp Phe Arg Ala Ala Pro Leu Ala Ala Ser Asp Leu Ala
225                 230                 235                 240

-continued

Gly Leu Pro Pro Ala Tyr Val Ile Thr Ala Gly Leu Asp Pro Leu Arg
            245                 250                 255

Asp Glu Gly Ala Gln Tyr Ala Glu Lys Leu Arg Glu Ala Gly Val Ala
        260                 265                 270

Val Glu His Val Gly Tyr Asp Asp Met Ile His Gly Phe Met Ser Met
        275                 280                 285

Ser Asn Ala Leu Asp Thr Ala Lys Leu Ala Ile Glu Arg Ala Gly Asp
290                 295                 300

Ala Leu Arg Asn Ala Leu Arg
305                 310

<210> SEQ ID NO 5
<211> LENGTH: 316
<212> TYPE: PRT
<213> ORGANISM: Unknown
<220> FEATURE:
<223> OTHER INFORMATION: Derived from metagenome

<400> SEQUENCE: 5

Met Ser Leu Asp Pro Lys Ala Arg Glu Leu Leu Ala Met Val Tyr Arg
1               5                   10                  15

Val Asn Ala Pro Arg Phe His Glu Leu Ser Val Ser Gln Ala Arg His
                20                  25                  30

Ala Thr Gln Lys Leu Met Phe Ala Phe Arg Pro Glu Ala Pro Ala Val
            35                  40                  45

Ala Ser Thr Thr Glu Val Pro Ile Pro Arg Pro Asp Gly Ser Val Leu
        50                  55                  60

Phe Ala Arg Leu Tyr Arg Pro Leu Gly Cys His Ala Ser Glu Asp Leu
65                  70                  75                  80

Gly Leu Leu Ile Tyr Phe His Gly Gly Gly Trp Cys Thr Gly Asp Leu
                85                  90                  95

Pro Gly Tyr Asp Val Leu Cys Arg Glu Leu Ala Asn Gln Ser Gly Ala
            100                 105                 110

Ala Val Leu Ser Val Asp Tyr Arg Leu Ala Pro Glu His Arg Phe Pro
        115                 120                 125

Ala Ala Val His Asp Ala Ser Leu Ala Phe Glu Trp Ser Thr Glu Asn
130                 135                 140

Ala Ser Leu Leu Gly Val Asp Ala Glu Arg Ile Ala Leu Gly Gly Asp
145                 150                 155                 160

Ser Ala Gly Gly Asn Leu Ala Ile Val Ala Leu Glu Ala Arg Asp
                165                 170                 175

Arg Ala Ala Arg Met Pro Arg Ala Leu Ala Leu Ile Tyr Pro Ser Thr
            180                 185                 190

Gln Ile His Ser Glu Arg Ser Ser Arg Glu Thr Phe Ala Asp Gly Tyr
        195                 200                 205

Phe Leu Asp Arg Glu Ser Leu Arg Trp Phe Tyr Glu His Tyr Phe Ala
    210                 215                 220

Asp Pro Ala Gln Ala Gln Ser Trp Gln Ala Ser Pro Met Leu Ala Ala
225                 230                 235                 240

Ser Leu Ala Gly Leu Pro Pro Ala Ile Leu Ile Thr Ala Gly Cys Asp
                245                 250                 255

Pro Leu Thr Asp Asp Cys Val Ala Phe Ala Glu Arg Met Val Ala Asp
            260                 265                 270

Gly Gly Leu Val Val Arg His His Phe Glu Gly Met Val His Gly Phe
        275                 280                 285

Leu Pro Leu Gly Lys Phe Phe Ala Gln Ala Asn Glu Ala Val Arg Cys
    290                 295                 300

Val Ser Ser Tyr Leu Arg Glu Ala Leu Gln Ala Ser
305                 310                 315

<210> SEQ ID NO 6
<211> LENGTH: 297
<212> TYPE: PRT
<213> ORGANISM: Unknown
<220> FEATURE:
<223> OTHER INFORMATION: Derived from metagenome
<220> FEATURE:
<221> NAME/KEY: misc_feature
<222> LOCATION: (216)..(216)
<223> OTHER INFORMATION: Xaa can be any naturally occurring amino acid

<400> SEQUENCE: 6

Met Ser Leu Glu Glu Leu Ala Val Val Arg Gln Leu Leu Ala Gly Leu
1               5                   10                  15

Val Thr Gly Glu Ala Arg Ser Leu Glu Asp Phe Arg Thr Ser Tyr Asp
            20                  25                  30

Glu Ala Gly Lys Ala Phe Gly Leu Pro Glu Gly Val Thr Val Thr Pro
        35                  40                  45

Val Ser Ala Gly Gly Val Pro Gly Glu Trp Leu Ala Pro Ala Ala Gly
    50                  55                  60

Ala Gly Lys Arg Val Leu Leu Tyr Leu His Gly Gly Tyr Ala Leu
65                  70                  75                  80

Gly Ser Leu Asp Ser His Arg His Leu Ala Ala His Thr Ala Leu Ala
                85                  90                  95

Leu Asn Gly Arg Val Leu Leu Ile Asp Tyr Arg Arg Ser Pro Glu His
            100                 105                 110

Pro Phe Pro Ala Ala Val Asp Asp Ala Leu Ala Ala Tyr Arg Trp Leu
        115                 120                 125

Thr Glu Thr Gly Val Asp Pro Ala Lys Leu Ala Val Ala Gly Asp Ser
    130                 135                 140

Ala Gly Gly Gly Leu Thr Val Ala Val Leu Leu Ala Ala Arg Asp Ala
145                 150                 155                 160

Gly Leu Arg Leu Pro Ala Ala Ala Val Cys Ile Ser Pro Trp Ala Asn
                165                 170                 175

Leu Glu Asn Lys Gly Ala Ser Tyr Gly Ala Lys Ala Asn Val Asp Pro
            180                 185                 190

Met Val Arg His Ala Asp Leu Glu Leu Trp Thr Ala Ala Tyr Leu Gly
        195                 200                 205

Thr Ser Thr Pro Arg Arg Ala Xaa Leu Ala Ser Pro Val Tyr Ala Asp
    210                 215                 220

Leu Asn Gly Leu Pro Pro Phe Leu Ile Gln Val Gly Ser Ser Glu Val
225                 230                 235                 240

Leu Leu Ser Asp Ser His Leu Leu Ala Asp Arg Leu Lys Glu Ala Gly
                245                 250                 255

Val Ser Val Asp Leu His Val Trp Pro Glu Met Ile His Val Trp His
            260                 265                 270

Trp Phe Ala Pro Val Leu Ser Glu Gly Arg Ala Ala Ile Asp Glu Met
        275                 280                 285

Ala Ser Phe Leu Asp Thr Lys Leu Gly
    290                 295

```
<210> SEQ ID NO 7
<211> LENGTH: 490
<212> TYPE: PRT
<213> ORGANISM: Unknown
<220> FEATURE:
<223> OTHER INFORMATION: Derived from metagenome

<400> SEQUENCE: 7

Met Thr Gly Leu His Phe Arg Ser Ala Ser Glu Leu Gly Arg Met Ile
1               5                   10                  15

Arg Arg Gly Glu Ile Ser Ser Ala Glu Leu Thr Asp His Phe Ile Gln
                20                  25                  30

Arg Ile Glu Thr Leu Asp Gly Lys Thr Asn Ala Val Val Ala Arg Asp
            35                  40                  45

Phe Asp Arg Ala Arg Ala Leu Ala Lys Glu Ala Asp Ala Ala Gln Ala
    50                  55                  60

Arg Gly Ala Ser Leu Gly Ala Leu His Gly Leu Pro Phe Thr Ile Lys
65                  70                  75                  80

Asp Ala Tyr Glu Val Glu Gly Ile Val Ser Thr Gly Gly Asn Pro Thr
                85                  90                  95

Trp Lys Asp His Val Pro Thr Ser Ser Ala Thr Ala Val Glu Arg Leu
            100                 105                 110

Gln Arg Ser Gly Ala Ile Val Met Gly Lys Thr Asn Val Pro Tyr Leu
        115                 120                 125

Ser Gly Asp Leu Gln Thr Tyr Asn Asp Ile Tyr Gly Thr Thr Asn Asn
130                 135                 140

Pro Trp Ala Leu Asp Cys Gly Pro Gly Ser Ser Gly Gly Ser Ala
145                 150                 155                 160

Ala Ser Leu Ala Ala Gly Phe Ala Ala Glu Phe Gly Ser Asp Ile
                165                 170                 175

Gly Gly Ser Ile Arg Thr Pro Ala His Leu Cys Gly Val Phe Gly His
            180                 185                 190

Lys Pro Ser Phe Gly Ile Val Pro Lys Arg Gly His Leu Ser Pro Pro
        195                 200                 205

Pro Gly Cys Leu Ser Glu Gly Asp Leu Ser Val Ala Gly Pro Leu Ala
210                 215                 220

Arg Ser Ala Glu Asp Leu Lys Leu Leu Leu Ser Leu Thr Ala Gly Pro
225                 230                 235                 240

Asp Trp Ala Asp Ala Ala Gly Trp Lys Leu Asp Leu Pro Ala Arg
                245                 250                 255

Ala Arg Thr Pro Arg Glu Leu Arg Ala Ala Val Trp Ile Asp Asp Glu
            260                 265                 270

Phe Cys Asp Ile Asp Arg Glu Ser Ala Asp Leu Leu Arg Asn Ala Ala
        275                 280                 285

Lys Ala Leu Gln Asp Ala Gly Ala Asn Val Asp Trp Asn Ala Arg Pro
    290                 295                 300

Asp Phe Thr Leu Ala Glu Ile Thr Glu Cys Tyr Leu Ile Leu Leu His
305                 310                 315                 320

Ser Gln Ile Gly Ala Gly Met Pro Gln Ser Ile Arg Asp His Trp Ala
                325                 330                 335

Glu Met Lys Lys Gly Phe Ala Pro Asp Asp Lys Ser His Ala Ala Leu
            340                 345                 350

Gln Ala Ile Gly Gly Thr Leu Ser Leu Ala Glu Arg Ala Val Trp Lys
        355                 360                 365

Glu Val Gln Ala Gln Leu Arg Trp Lys Trp His Thr Phe Phe Lys Ser
```

```
            370                 375                 380
Tyr Asp Val Val Leu Ser Pro Val Leu Met Arg Pro Ala Phe Glu His
385                 390                 395                 400

Asn His Gln Ser Asn Trp His Lys Arg Glu Leu Asp Val Asn Gly Val
                405                 410                 415

Lys Arg Pro Tyr Met Asp Val Leu Ile Trp Ala Gly Pro Ala Val Val
            420                 425                 430

Ser Tyr Leu Pro Ala Thr Ala Ala Pro Val Gly Val Thr Ser Glu Gly
            435                 440                 445

Lys Pro Val Gly Ile Gln Ile Ile Gly Pro His Leu Glu Asp Tyr Thr
            450                 455                 460

Thr Ile Ala Val Ala Gly Met Phe Glu Ile Leu Gly Gly Phe Lys
465                 470                 475                 480

Pro Pro Lys Gly Trp Ala Ala Ala Leu Glu
                485                 490

<210> SEQ ID NO 8
<211> LENGTH: 177
<212> TYPE: PRT
<213> ORGANISM: Unknown
<220> FEATURE:
<223> OTHER INFORMATION: Derived from metagenome

<400> SEQUENCE: 8

Cys Ala Cys Cys Leu Ser Leu Val Asp Arg Asp Gly Arg Arg Pro Gly
1               5                   10                  15

Glu Leu Ala Val Ala Gly Asp Ser Ala Gly Gly Gly Leu Thr Val Ala
            20                  25                  30

Val Leu Leu Ala Ala Arg Asp Ala Gly Leu Arg Leu Pro Ala Ala Ala
        35                  40                  45

Val Cys Ile Ser Pro Trp Ala Asn Leu Glu Asn Lys Gly Ala Ser Tyr
    50                  55                  60

Gly Ala Lys Ala Asn Val Asp Pro Met Val Arg His Ala Asp Leu Glu
65                  70                  75                  80

Leu Trp Thr Ala Ala Tyr Leu Gly Thr Ser Thr Pro Arg Arg Ala Pro
                85                  90                  95

Leu Ala Ser Pro Val Tyr Ala Asp Leu Asn Gly Leu Pro Pro Phe Leu
            100                 105                 110

Ile Gln Val Gly Ser Ser Glu Val Leu Leu Ser Asp Ser His Leu Leu
        115                 120                 125

Ala Asp Arg Leu Lys Glu Ala Gly Val Ser Val Asp Leu His Val Trp
    130                 135                 140

Pro Glu Met Ile His Val Trp His Trp Phe Ala Pro Val Leu Ser Glu
145                 150                 155                 160

Gly Arg Ala Ala Ile Asp Glu Met Ala Ser Phe Leu Asp Thr Lys Leu
                165                 170                 175

Gly

<210> SEQ ID NO 9
<211> LENGTH: 491
<212> TYPE: PRT
<213> ORGANISM: Unknown
<220> FEATURE:
<223> OTHER INFORMATION: Derived from metagenome

<400> SEQUENCE: 9

Leu Glu Arg Ser Asp Leu Asp Tyr Ala Ser Ala Thr Glu Ile Ala Arg
```

-continued

```
1               5                   10                  15
Leu Val Arg Thr Arg Gln Ile Ser Ala Ala Asp Val Thr Glu His Ala
                20                  25                  30

Ile Ser Arg Ile Glu Ala Arg Asn Gly Ser Leu Asn Ala Phe Val Tyr
                35                  40                  45

Thr Asp Phe Glu Gln Ala Arg Ser Arg Ala Lys Asp Leu Asp Thr Arg
                50                  55                  60

Ile Ser Ala Gly Glu Asp Val Gly Pro Leu Ala Gly Val Pro Thr Ala
65                  70                  75                  80

Ile Lys Asp Leu Phe Asn Phe Tyr Pro Gly Trp Pro Ser Thr Leu Gly
                85                  90                  95

Gly Ile Arg Cys Leu Arg Asp Phe Lys Leu Asp Val Lys Ser Arg Tyr
                100                 105                 110

Ala Thr Lys Met Glu Glu Ala Gly Ala Val Val Leu Gly Ile Thr Asn
                115                 120                 125

Ser Pro Val Leu Gly Phe Arg Gly Thr Thr Asp Asn Asp Leu Tyr Gly
                130                 135                 140

Pro Thr Arg Asn Pro Phe Asp Leu Ser Arg Asn Ser Gly Gly Ser Ser
145                 150                 155                 160

Gly Gly Thr Ser Ala Ala Val Ala Asp Gly Leu Leu Pro Ile Gly Asp
                165                 170                 175

Gly Thr Asp Gly Gly Gly Ser Ile Arg Ile Pro Ala Ala Trp Cys His
                180                 185                 190

Val Phe Gly Phe Gln Ala Ser Pro Gly Arg Ile Pro Leu Ala Ile Arg
                195                 200                 205

Pro Asn Ala Phe Gly Ala Ala Ala Pro Phe Ile Tyr Glu Gly Pro Ile
                210                 215                 220

Thr Arg Thr Val Glu Asp Ala Ala Leu Ala Met Ser Val Leu Ala Gly
225                 230                 235                 240

Ser Asp Pro Ala Asp Pro Phe Ser Leu Asn Asp Arg Leu Asp Trp Leu
                245                 250                 255

Gly Ala Val Asp Gln Pro Ile Thr Ser Leu Arg Ile Gly Phe Thr Pro
                260                 265                 270

Asp Phe Gly Gly Phe Pro Val Glu Pro Ala Val Ala Ala Thr Ile Ala
                275                 280                 285

His Ala Val Arg Ala Phe Glu Gln Ala Gly Ala Lys Ile Val Pro Leu
                290                 295                 300

Lys Leu Asp Phe Gly Tyr Thr His Asp Glu Leu Ser Gln Leu Trp Cys
305                 310                 315                 320

Arg Met Ile Ser Gln Gly Thr Ile Ala Val Val Asp Ser Phe Ala Glu
                325                 330                 335

Asn Gly Leu His Leu Glu Pro Asp Phe Pro Ala Pro Val Met Glu Trp
                340                 345                 350

Ala Gln Lys Ala Lys Asn Ala Thr Pro Leu Asp Leu His Arg Asp Gln
                355                 360                 365

Val Met Arg Thr Lys Val Tyr Asp Val Leu Asn Ala Ala Phe Ser Gln
                370                 375                 380

Val Asp Leu Ile Ala Gly Pro Thr Thr Thr Cys Leu Pro Thr Pro Asn
385                 390                 395                 400

Gly Glu Arg Gly Met Thr Val Gly Pro Ser Glu Ile Ala Gly Thr Pro
                405                 410                 415

Ile Asn Arg Leu Ile Gly Phe Cys Pro Thr Phe Leu Thr Asn Phe Thr
                420                 425                 430
```

```
Gly Asn Pro Ala Ala Ser Leu Pro Ala Gly Leu Ala Asp Gly Leu Pro
        435                 440                 445

Val Gly Leu Met Leu Ile Gly Pro Arg Arg Asp Asp Leu Thr Val Leu
450                 455                 460

Ser Ala Ser Ala Ala Phe Glu Arg Val Gln Pro Trp Ala Asp Ser Tyr
465                 470                 475                 480

Arg Ile Pro Ala Ala Arg Pro Leu Gly Ser Gln
                485                 490

<210> SEQ ID NO 10
<211> LENGTH: 330
<212> TYPE: PRT
<213> ORGANISM: Unknown
<220> FEATURE:
<223> OTHER INFORMATION: Derived from metagenome

<400> SEQUENCE: 10

Met Arg Pro Arg Ser Arg Pro His Ala Arg Ala Arg Gly Ala Pro Thr
1               5                   10                  15

Ile Leu Arg Asp Pro Ala Thr Met Ala Leu His Arg Thr Pro Arg Arg
            20                  25                  30

Asn Asp Met Ala Asp Arg Gly Ile Glu Val Val His Ala His Leu Ala
        35                  40                  45

Lys Leu Pro Pro Ala Asp Ser Leu Thr Val Ala Glu Arg Arg Ala Gln
    50                  55                  60

Tyr Glu Arg Ala Glu Lys Val Phe Pro Leu Ser Pro Asp Val Lys Val
65                  70                  75                  80

Glu Arg Val Thr Ala Gly Ala Ala Pro Ala Glu Trp Leu Arg Pro Pro
                85                  90                  95

Ser Ala Arg Ala Gly His Val Val Leu Tyr Leu His Gly Gly Gly Tyr
            100                 105                 110

Val Ile Gly Ser Pro Arg Ser His Arg His Leu Ala Ala Ala Ile Ala
        115                 120                 125

Gly Ala Ala Gly Thr Asn Ala Leu Leu Leu Asp Tyr Arg Leu Ala Pro
    130                 135                 140

Glu His Pro Phe Pro Ala Ala Leu Asp Asp Ala Val Ala Ala Tyr Arg
145                 150                 155                 160

Trp Leu Leu Asp Gln Gly Ile Ala Ala Glu His Ile Ala Val Ala Gly
                165                 170                 175

Asp Ser Ala Gly Gly Gly Leu Thr Val Ala Thr Leu Leu Ala Leu Arg
            180                 185                 190

Asp Ala His Leu Pro Arg Pro Ala Ala Gly Val Cys Ile Ser Pro Trp
        195                 200                 205

Val Asp Leu Thr Cys Ser Gly Gly Ser Tyr Gln Ser Lys Ala Gly Val
    210                 215                 220

Asp Pro Ile Val Arg Gln Ala Gly Val Ala Glu Met Ala Arg Ala Tyr
225                 230                 235                 240

Leu Gly Ala Thr Asp Pro Arg Ser Pro Leu Ala Ser Pro Leu Phe Ala
                245                 250                 255

Asp Leu Arg Gly Leu Pro Pro Leu Ile His Val Gly Ser Asp Glu
            260                 265                 270

Val Leu Leu Asp Asp Ala Ile Gly Leu Ala Glu Arg Ala Lys Ala Ala
        275                 280                 285

Gly Val Asp Ala Thr Leu Glu Gln Trp Asp Arg Met Ile His Val Trp
    290                 295                 300
```

His Trp Phe Leu Pro Met Leu Asp Glu Ala Gln Thr Ala Val Glu Ser
305                 310                 315                 320

Ile Gly Arg Phe Val Arg Ala Arg Thr Ala
                325                 330

<210> SEQ ID NO 11
<211> LENGTH: 544
<212> TYPE: PRT
<213> ORGANISM: Pig

<400> SEQUENCE: 11

Gly Gln Pro Ala Ser Pro Val Val Asp Thr Ala Gln Gly Arg Val
1               5                   10                  15

Leu Gly Lys Tyr Val Ser Leu Glu Gly Leu Ala Gln Pro Val Ala Val
                20                  25                  30

Phe Leu Gly Val Pro Phe Ala Lys Pro Pro Leu Gly Ser Leu Arg Phe
                35                  40                  45

Ala Pro Pro Gln Pro Ala Glu Pro Trp Ser Phe Val Lys Asn Thr Thr
50                  55                  60

Ser Tyr Pro Pro Met Cys Cys Gln Asp Pro Val Ala Gly Gln Met Thr
65                  70                  75                  80

Ser Asp Leu Phe Thr Asn Arg Lys Glu Arg Leu Ile Pro Glu Phe Ser
                85                  90                  95

Glu Asp Cys Leu Tyr Leu Asn Ile Tyr Thr Pro Ala Asp Leu Thr Lys
                100                 105                 110

Arg Gly Arg Leu Pro Val Met Val Trp Ile His Gly Gly Gly Leu Val
                115                 120                 125

Val Gly Gly Ala Ser Thr Tyr Asp Gly Leu Ala Leu Ala Ala His Glu
130                 135                 140

Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
                165                 170                 175

Gln Val Ala Ala Leu His Trp Val Gln Glu Asn Ile Ala Asn Phe Gly
                180                 185                 190

Gly Asp Pro Gly Ser Val Thr Ile Phe Gly Glu Ser Ala Gly Gly Glu
                195                 200                 205

Ser Val Ser Val Leu Val Leu Ser Pro Leu Ala Lys Asn Leu Phe His
210                 215                 220

Arg Ala Ile Ser Glu Ser Gly Val Ala Phe Thr Ala Gly Leu Val Arg
225                 230                 235                 240

Lys Asp Met Lys Ala Ala Ala Lys Gln Ile Ala Val Leu Ala Gly Cys
                245                 250                 255

Lys Thr Thr Thr Ser Ala Val Phe Val His Cys Leu Arg Gln Lys Ser
                260                 265                 270

Glu Asp Glu Leu Leu Asp Leu Thr Leu Lys Met Lys Phe Phe Ala Leu
                275                 280                 285

Asp Leu His Gly Asp Pro Arg Glu Ser His Pro Phe Leu Thr Thr Val
                290                 295                 300

Val Asp Gly Val Leu Leu Pro Lys Met Pro Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly

```
            340                 345                 350
Lys Leu Asp Gln Lys Thr Ala Thr Ser Leu Leu Trp Lys Ser Tyr Pro
            355                 360                 365

Ile Ala Asn Ile Pro Glu Glu Leu Thr Pro Val Ala Thr Asp Lys Tyr
        370                 375                 380

Leu Gly Gly Thr Asp Pro Val Lys Lys Asp Leu Phe Leu Asp
385                 390                 395                 400

Leu Met Gly Asp Val Val Phe Gly Val Pro Ser Val Thr Val Ala Arg
                405                 410                 415

Gln His Arg Asp Ala Gly Ala Pro Thr Tyr Met Tyr Glu Phe Gln Tyr
            420                 425                 430

Arg Pro Ser Phe Ser Ser Asp Lys Lys Pro Lys Thr Val Ile Gly Asp
        435                 440                 445

His Gly Asp Glu Ile Phe Ser Val Phe Gly Ala Pro Phe Leu Arg Gly
            450                 455                 460

Asp Ala Pro Glu Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
                485                 490                 495

His Trp Pro Met Tyr Asp Gln Glu Glu Gly Tyr Leu Gln Ile Gly Val
            500                 505                 510

Asn Thr Gln Ala Ala Lys Arg Leu Lys Gly Glu Glu Val Ala Phe Trp
        515                 520                 525

Asn Asp Leu Leu Ser Lys Glu Ala Ala Lys Lys Pro Pro Lys Ile Lys
    530                 535                 540

<210> SEQ ID NO 12
<211> LENGTH: 342
<212> TYPE: PRT
<213> ORGANISM: Candida sp.

<400> SEQUENCE: 12

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
        35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

Thr Ala Leu Tyr Ala Gly Ser Gly Asn Asn Lys Leu Pro Val Leu Thr
        115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175
```

```
Pro Ser Val Trp Gln Gln Thr Thr Gly Ser Ala Leu Thr Thr Ala Leu
            180             185                 190

Arg Asn Ala Gly Gly Leu Thr Gln Ile Val Pro Thr Thr Asn Leu Tyr
        195             200             205

Ser Ala Thr Asp Glu Ile Val Gln Pro Gln Val Ser Asn Ser Pro Leu
        210             215             220

Asp Ser Ser Tyr Leu Phe Asn Gly Lys Asn Val Gln Ala Gln Ala Val
225             230             235             240

Cys Gly Pro Leu Phe Val Ile Asp His Ala Gly Ser Leu Thr Ser Gln
                245             250             255

Phe Ser Tyr Val Val Gly Arg Ser Ala Leu Arg Ser Thr Thr Gly Gln
            260             265             270

Ala Arg Ser Ala Asp Tyr Gly Ile Thr Asp Cys Asn Pro Leu Pro Ala
            275             280             285

Asn Asp Leu Thr Pro Glu Gln Lys Val Ala Ala Ala Leu Leu Ala
        290             295             300

Pro Ala Ala Ala Ile Val Ala Gly Pro Lys Gln Asn Cys Glu Pro
305             310             315             320

Asp Leu Met Pro Tyr Ala Arg Pro Phe Ala Val Gly Lys Arg Thr Cys
                325             330             335

Ser Gly Ile Val Thr Pro
            340
```